April 18, 1972 P. ECKE Plant Pat. 3,119
POINSETTIA PLANT
Filed March 11, 1970
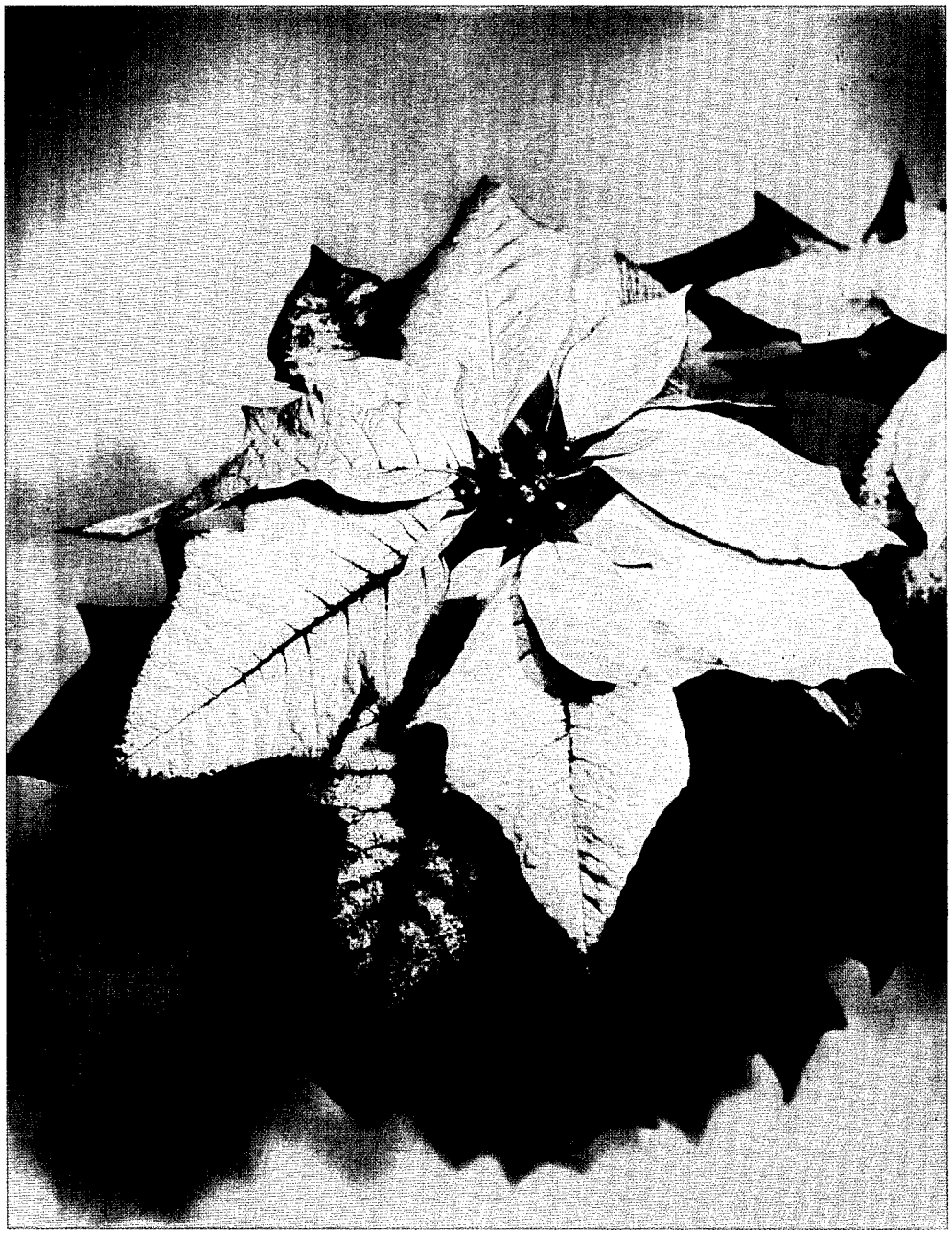
Inventor.
Paul Ecke
By: Robb & Robb
Attorneys.

United States Patent Office

Plant Pat. 3,119
Patented Apr. 18, 1972

3,119
POINSETTIA PLANT

Paul Ecke, Encinitas, Calif., assignor to Paul Ecke Inc., Encinitas, Calif.

Filed Mar. 11, 1970, Ser. No. 18,771
Int. Cl. A01h 5/00
U.S. Cl. Plt.—86 1 Claim The present invention relates to a new and distinct variety of poinsettia plant (botanically known as *Euphorbia pulcherrima*), which was originated by me by crossing an unnamed and unpatented poinsettia variety of unidentified parentage with another unnamed poinsettia variety also of unidentified parentage.

As a result of this breeding, I have produced a new poinsettia variety which is similar in many respects to the variety known as #C–1 (Plant Patent No. 2,923), but which primarily differs therefrom by having creamy white bracts instead of the normal red bracts of #C–1, thereby combining the following unique and commercially valuable characteristics which are outstanding therein and which distinguish my new variety from all other poinsettia varieties of which I am aware:

(1) An ability to propagate very well by vegetative cuttings;
(2) A very vigorous, tough, and durable plant habit of medium height and having the ability to grow well as a multiple stem and multiple bloom plant;
(3) A very vigorous and extensive root system;
(4) A good branching habit;
(5) Stiff stems which do not require staking;
(6) Very pointed and attractive dark green foliage;
(7) Many very wide bracts which give the plant a full and complete appearance;
(8) Retention of the bracts, foliage and inflorescences for an unusually long period of time after reaching maturity;
(9) A habit of not requiring light to delay bud set;
(10) A habit of setting buds quite easily under higher night temperatures and longer day lengths than other poinsettia varieties;
(11) A good pinching habit which produces 3 or more breaks;
(12) A normally later blooming habit than other varieties, but having the ability to be satisfactorily brought into bloom and full maturity in every month of the year through the exercise of proper greenhouse cultural techniques;
(13) A distinctive and attractive slightly ruffled appearance of the bracts and their absence of any tendency to droop with age;
(14) A distinctive and attractive creamy white bract color;
(15) Absence of drooping and retention of the inflorescence position relative to the bracts without rising as occurs in other varieties as the inflorescences approach maturity; and
(16) Excellent keeping qualities with consequent suitability for home decoration.

Asexual reproduction of my new variety by vegetative cuttings propagated under mist at Encinitas, Calif., shows that the foregoing characteristics and distinctions come true to form and are established and transmitted through succeeding propagations.

The accompanying drawing shows a typical specimen plant of my new variety as depicted in color as nearly true as it is reasonably possible to make the same in a color illustration of this character.

The following is a detailed description of my new poinsettia variety, with color terminology in accordance with Wilson's Horticultural Colour Chart, except where general color terms of ordinary dictionary significance are obvious, as based on specimens grown at Encinitas, Calif., under regular commercial practices:

Parentage: Seedling.
*Seed parent.*—An unnamed seedling of unidentified parentage.
*Pollen parent.*—An unnamed seedling of unidentified parentage.

Propagation: Holds its distinguishing characteristics through succeeding propagations by vegetative cuttings; propagates very well.

Form: Medium tall; upright; well-branched; graceful contour.

Habit of growth: Vigorous.

Rooting habit: Very fast (from 12 to 15 days under mist); vigorous; extensive; uniform.

Blooming habit: Approximately 10 to 11 weeks after start of short days.

Blooming season: Naturally in December, but has excellent suitability for forcing in every month of the year by appropriate greenhouse culture practices.

Foliage: Alternate; borne horizontally on stems; persistent; abundant.
*Size.*—Medium; borne on short petioles; from about 3 inches to 6 inches long; from about 2½ inches to 5 inches wide.
*Shape.*—Little serration; wide at base; very pointed at tip.
*Texture.*—Upper side—medium glossy; medium smooth; with ordinary recessed veins. Under side—dull; with ordinary protruding veins.
*Margin.*—Well defined.
*Color.*—New foliage—Upper side—Near Scheele's Green, Plate 860, page 175. Lower side—Near Scheele's Green, Plate 860/1, page 175. Old foliage—Upper side—Near Ivy Green, Plate 0001060, page 200. Lower side—Near Leek Green, Plate 000858, page 197.

Disease resistance: Resistant to rhizoctonia and pythium stem and root rot during propagation and growing period, and very resistant to botrytis during blooming period, as determined by comparison with other plants grown under the same cultural conditions at Encinitas, Calif., which are infested with these diseases.

Bracts: Many (approximately 15 to 20); very wide; excellent retention; new bracts form and develop as other bracts mature; very long lasting; short pointed when young, but becoming long pointed at maturity; retain relative position and do not droop when mature or as bracts continue to age; retain their color exceptionally well; slightly ruffled in appearance; have short petioles giving bracets a full appearance; tight center giving influorescence form which is attractive in appearance. Color—creamy white, corresponding to near Canary Yellow, Plate 2/3, page 2.

Flowers:
*Borne.*—Continuously for several months; many flowers per stem in regular clusters in varying stages of development; borne on strong, very short stems; slow development, giving a compact appearance for a greater period of time; position of the flowers remains relatively low without rising as it does in other commercial varieties during early development, and does not spread out during later stages of development, thereby giving a more attractive appearance for a longer period of time.
*Quantity of bloom.*—Relatively abundant; continuous; flowers gradually drop off after maturity.
*Buds.*—From medium to large size; borne on light green stems. Color—Near Lettuce Green, Plate 861/3, page 176.

*General observations*

The new poinsettia variety is very similar in most respects to the variety #C–1, but primarily differs therefrom by having creamy white bracts instead of the normal red bracts of #C–1, thereby achieving a new and distinct combination of characteristics not found in any other poinsettia variety.

I claim:

1. A new and distinct variety of poinsettia plant, substantially as herein shown and described, characterized particularly as to novelty by the unique combination of an ability to propagate very well by vegetative cuttings, a very vigorous, tough and durable plant habit of medium height and having the ability to grow well as a multiple stem and multiple bloom plant, a very vigorous and extensive root system, a good branching habit, stiff stems which do not require staking, very pointed and attractive dark green foliage, many very wide bracts which give the plant a full and complete appearance, retention of the bracts, foliage and influorescences for an unusually long period of time after reaching maturity, a habit of not requiring light to delay bud set, a habit of setting buds quite easily under higher night temperatures and longer day lengths than other poinsettia varieties, a good pinching habit which produces 3 or more breaks, a normally later blooming habit than other varieties, but having the ability to be satisfactorily brought into bloom and full maturity in every month of the year through the exercise of proper greenhouse cultural techniques, a distinct and attractive slightly ruffled appearance of the bracts and their absence of any tendency to droop with age, a distinctive and attractive creamy white bract color, absence of drooping and retention of the influorescence position relative to the bracts without rising as occurs in other varieties as the inflorescences approach maturity, and excellent keeping qualities with consequent suitability for home decoration.

No references cited.

ROBERT E. BAGWILL, Primary Examiner